US00PP35670P2

(12) United States Plant Patent
Sauter et al.

(10) Patent No.: US PP35,670 P2
(45) Date of Patent: Mar. 5, 2024

(54) PINEAPPLE PLANT NAMED 'FR11834'

(50) Latin Name: *Ananas comosus*
Varietal Denomination: FR11834

(71) Applicant: Del Monte International GmbH, Zug (CH)

(72) Inventors: Hans Sauter, Coral Gables, FL (US); Joao Rodrigues, Limoeiro do Norte (BR); Ebrahim Firoozabady, Pleasant Hill, CA (US)

(73) Assignee: Del Monte International GmbH, Zug (CH)

( * ) Notice: Subject to any disclaimer, the term of this patent is extended or adjusted under 35 U.S.C. 154(b) by 0 days.

(21) Appl. No.: 17/978,840

(22) Filed: Nov. 1, 2022

(51) Int. Cl.
*A01H 5/08* (2018.01)
*A01H 6/22* (2018.01)

(52) U.S. Cl.
USPC ..... Plt./156

(58) Field of Classification Search
USPC ..... Plt./156
CPC ..... A01H 5/08; A01H 5/00; A01H 6/22
See application file for complete search history.

(56) References Cited

U.S. PATENT DOCUMENTS

PP16,328 P3 * 3/2006 Morales ..... A01H 6/22
Plt./156

OTHER PUBLICATIONS

Malta, C., et al. "Use of Gras Substances to Control the Growth of the Phytopathogen Fusarium Guttiforme in Vitro," Jornada de Iniciacao Cientifica e Extensao; 7 pages. With Machine Translation.
Matos, A., et al., "Pineapple Varieties Resistant to Fusarious Disease," 6 pages. With Machine Translation.
Nogueira, S., et al., "Fungicides in the control of pineapple fusariosis in the state of Tocantins, Brazil," Journal of Agricultural Sciences, 2014 37(4); 447-455; 10 pages. With Machine Translation.

* cited by examiner

*Primary Examiner* — June Hwu
(74) *Attorney, Agent, or Firm* — Dickinson Wright PLLC; Kristopher Lance Anderson

(57) ABSTRACT

A new and distinct pineapple plant named 'FR11834', comprising certain unique traits, standing out *Fusarium* resistance obtained after crossing and backcrossing *Fusarium* resistant pineapple lines with an MD-2 pineapple. The invention incorporates stable, inheritable resistance to *Fusariosis* disease in a pineapple variety capable of addressing all of the high quality requirements of global export markets.

6 Drawing Sheets

Genus and species: *Ananas comosus.*

Figure 1:
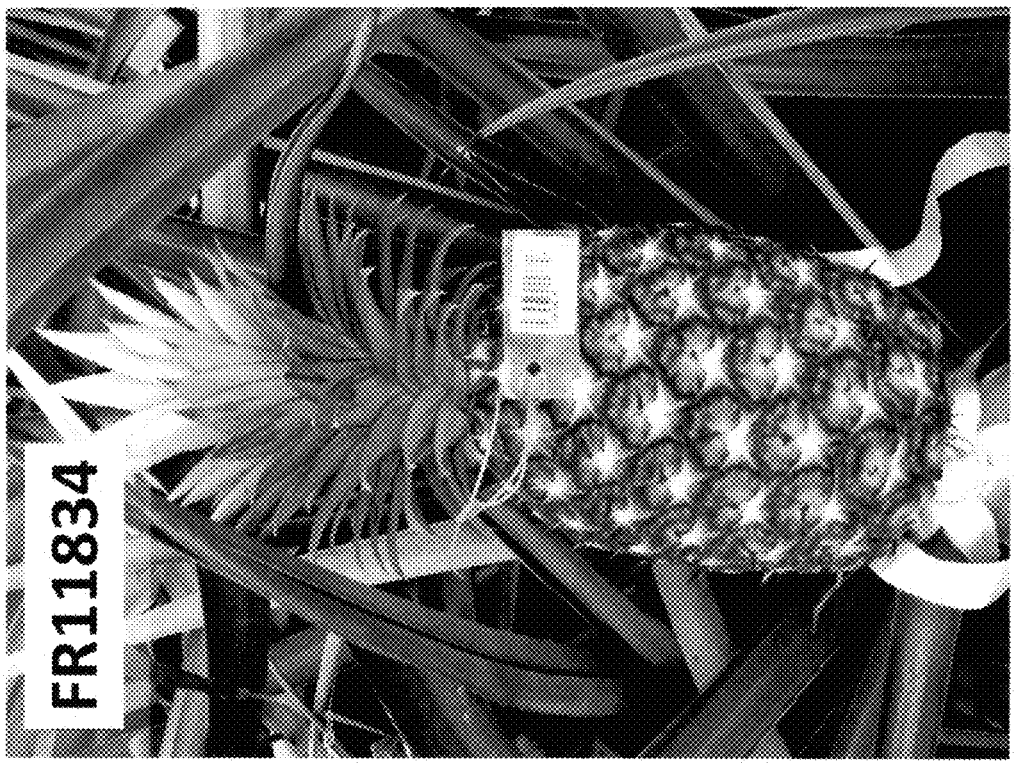

Variety denomination: 'FR11834'.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

Inventors: Hans Sauter, Joao Rodrigues and Ebrahim Firoozabady.

BACKGROUND OF THE NEW PLANT

The present invention comprises a new and distinct pineapple variety of *Ananas comosus*, hereinafter referred to as the variety named 'FR11834'. The said variety has been developed by sexual crossing between plants of Manzana variety (not patented) and the variety 'MD-2' (non-patented), and selected from large populations of progenies of hybrids (F1), backcrossed three times (BC1, BC2 and BC3). This process started in 2009 in Limoeiro do Norte, Ceará, Brazil, and took thirteen consecutive years of iterative hybridization, selection, and planting. The new variety 'FR11834' in particular was the result of the back-cross of a selected plant of the '1/2.24' line, with a selected plant of 'MD-2', to achieve the combination of characters of interest that qualify 'FR11834' as a variety of commercial potential.

The main objective of the hybridization program was to introduce stable resistance to *Fusariosis* disease of pineapples into a variety that would produce attractive fruits with excellent organoleptic traits and the right shape and size that would satisfy the strict requirements of export markets. The new cultivar 'FR11834' is being reproduced asexually, faithful to the type through the tissue culture technique in Limoeiro do Norte, Ceará, Brazil.

BACKGROUND INFORMATION ABOUT THE DISEASE

Among all the diseases of pineapple (*Ananas comosus* var. *comosus*), *Fusariose* caused by *Fusarium guttiforme* stands out for being the one that brings largest economic losses to producers, with estimated losses between 50% and 100% of fruits and up to 50% in propagules (Matos, 2008).

*Fusarium guttiforme* can infect all parts of the pineapple causing the exudation of a gummy substance from the affected tissues. In plants, the lesion is located on the stem and progresses to the base of the leaf being restricted to the achlorophyllous region. Under field conditions an infected pineapple plant may show one or more external symptoms: stem tilt to the side where the lesion is located; changes in plant phyllotaxis, increasing the number of leaves per spiral; changes in the architecture of the plant that has the appearance of a funnel or cup; reduction in leaf length as well as in the overall development of the plant; "opening" of the central rosette of plants showing the youngest leaves; reducing the stem development; chlorosis; death of the apical meristem. As the disease progresses, the plant paralyzes growth and dies (Matos & Junghans, 2006).

In the fruits, the symptoms are manifested in the form of soft rot in the pulp, with accumulation of gum in the ovules of the ovary and exudation of the same through the infected floral cavity. At a more advanced stage of disease development, the skin of the fruit in the infected areas presents a red brown coloration and are at the lower level. These symptoms are observed with greater intensity in fruits near harvest (Matos & Junghans, 2006).

Following extensive field and laboratory research, four isolates of *Fusarium guttiforme* were identified for their particularly high virulence in the North East of Brazil, subsequently isolated and reproduced to serve as standard inoculum for the resistance trials the pineapple hybrids participating in this project were subjected to.

SUMMARY OF THE INVENTION

The invention is related to a new and distinct pineapple variety of the Bromeliaceae family, which was derived from a backcross (BC3) between the 'MD-2' and the '1/2.24' (which in turn was already a backcross of a backcross between 'MD-2' X 'Manzana' cultivar), through hand pollination and mass selection process during thirteen years, and provides *Fusarium* resistance to pineapple plants that could be grown in all areas, including where the disease caused by *Fusarium guttiforme* occurs.

In most characteristics, the selected hybrid is more alike to the 'MD-2' parent than the '1/2.24' parent. The main difference is in the resistance to *Fusarium guttiforme* exhibited by the 'FR11834' and absent in the 'MD2' variety. The selected backcross 3 (BC3) plant's fruit has an internal quality and pulp color like the 'MD-2' fruit: the total soluble solid contents (TSS), citric acid, ascorbic acid, yellow pulp color, and the size of the fruit are like the 'MD-2'. In addition, the 'FR11834' fruit is cylindrical in shape, and has a very pleasant aroma, and delectable taste, just like the 'MD-2' variety.

Applicant has previously filed for patent for FR4139 (co-pending Plant patent application Ser. No. 17/963,093), another *Fusarium* resistant variety product of this program, however, in contrast to that said variety, 'FR11834' exhibits consistently higher sugar levels in the fruit pulp, and a yellowish coloration of the inflorescence in its early cone stage, prior to flower opening. The new variety is characterized by occasional presence of spines at the leaf tip. Leaf color is gray-green, similar to the color of both parental lines, 'MD-2', and the BC2 'Manzana' hybrid '1/2.24' (FIG. 1).

BRIEF DESCRIPTION OF THE PHOTOGRAPHS

The accompanying pictures illustrate the overall appearance of the new *Ananas comosus* var. *comosus* 'FR11834' showing infection damage caused by artificial inoculation with four different isolates of *Fusarium guttiforme* showing the colors as reasonably possible with colored reproductions of this type. The lesion caused by direct inoculation with an infected needle on the fruit helped verify the resistance trait (earlier established by immersion of young plants in a suspension of *Fusarium guttiforme's* most virulent isolate), when comparing reaction of fruit pulp tissue of the new pineapple variety 'FR11834' with 'MD2':

FIG. 1. View of the new variety 'FR11834' at 5.3 months after forcing (MAF).

Figure 2:
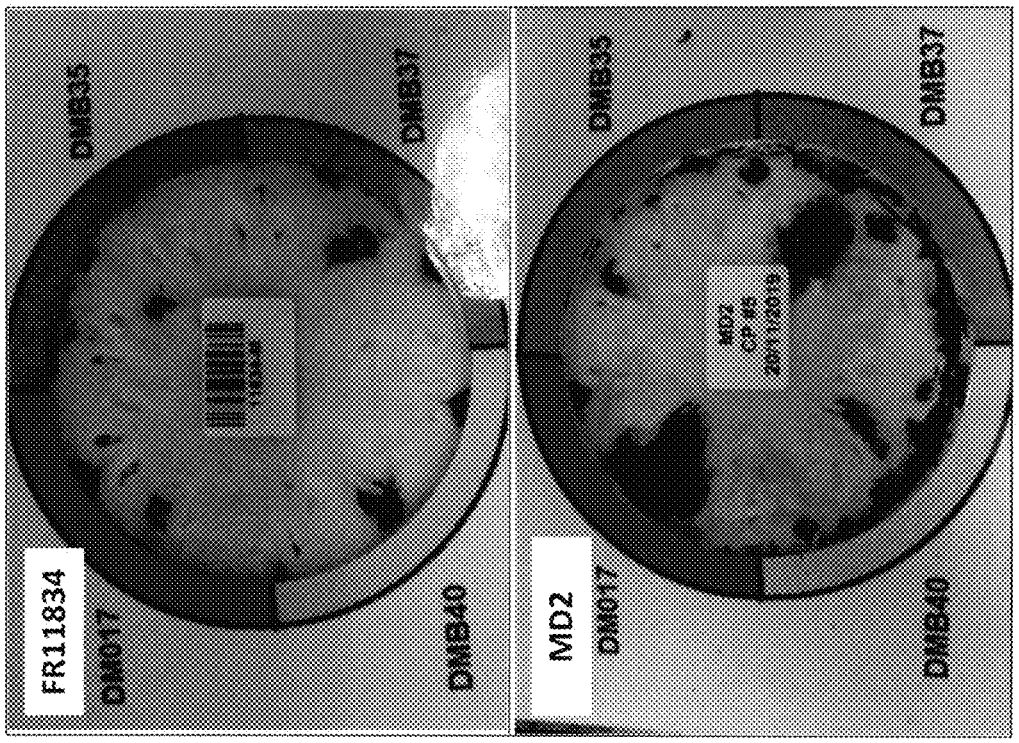

FIG. 2. Cross sectional view of 'FR11834' and 'MD2' fruit inoculated with *Fusarium guttiforme* isolates DM017, DMB35, DMB37 and DMB40 at 5.3 MAF.

Figure 3:
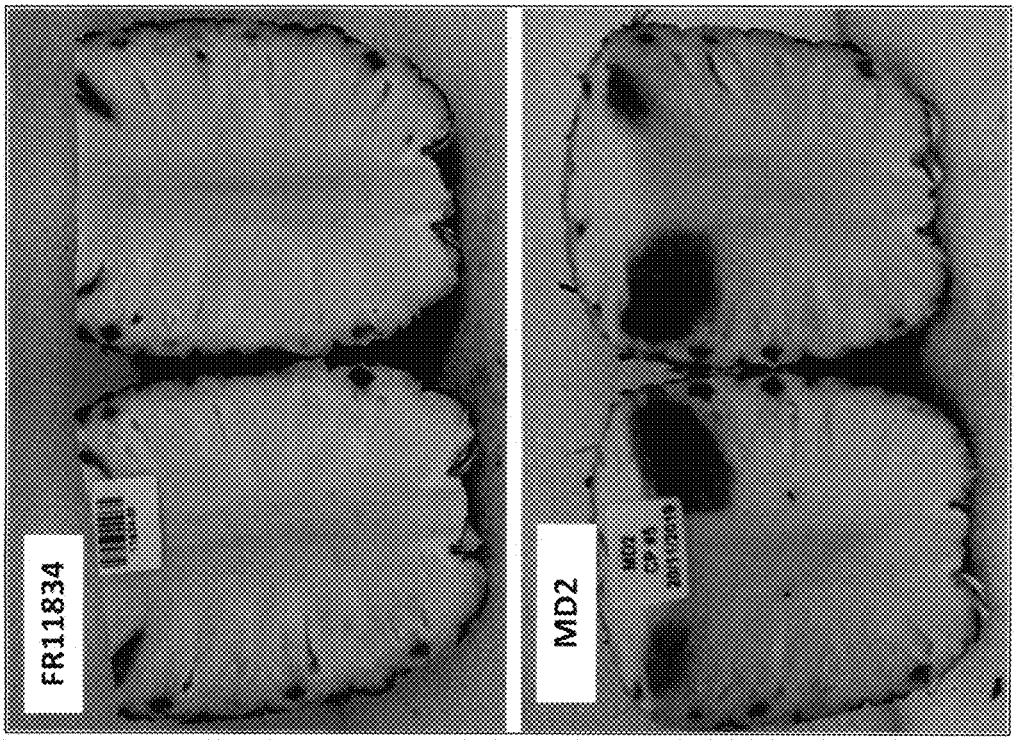

FIG. 3. Longitudinal section view of *Fusarium guttiforme* inoculation site on fruit of 'FR11834' variety (which may be denoted as 'FR11834-M') and 'MD2' fruit at 5.3 MAF.

Figure 4:
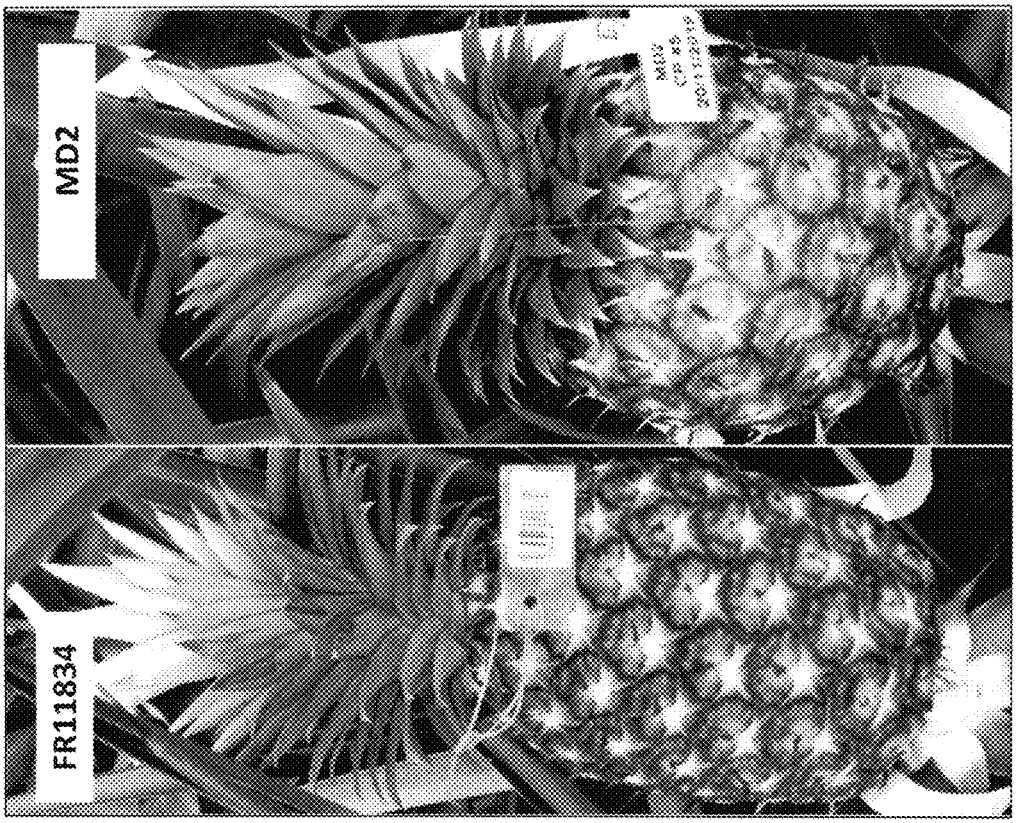

FIG. 4. External view of Fusarium guttiforme inoculation site on fruit of 'FR11834' and MD2 varieties at 5.3 MAF.

Figure 5:
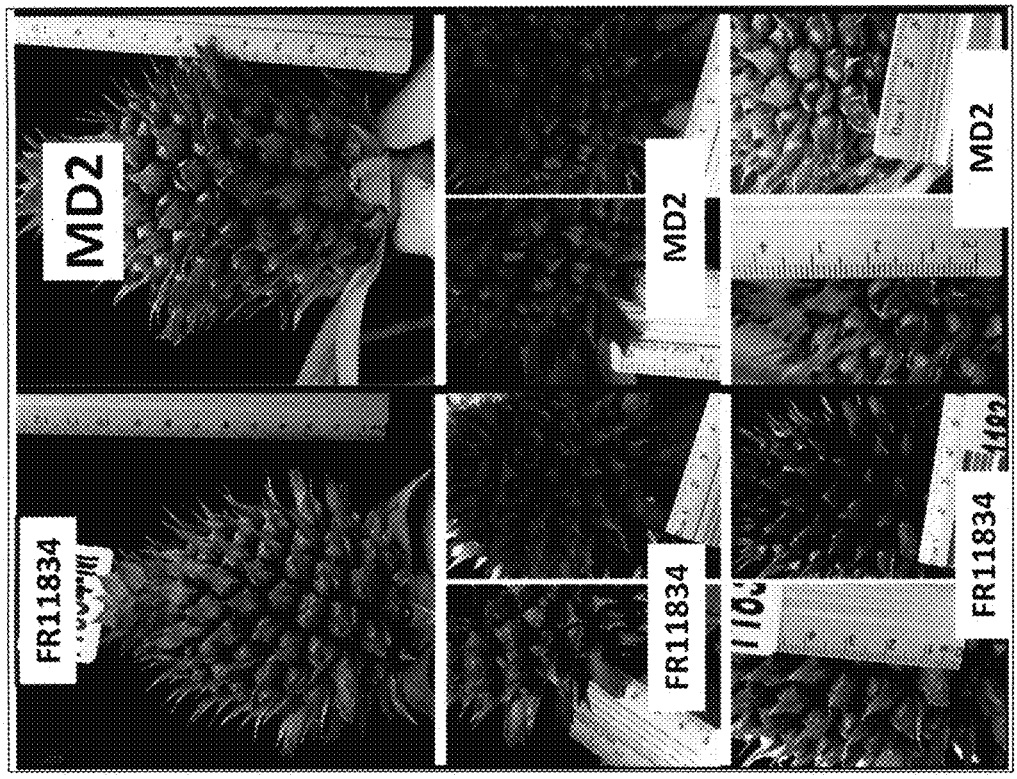

FIG. 5. External view of inflorescence of 'FR11834' (which may be denoted as 'FR11834-M') and MD2 varieties at 62 days after floral induction.

Figure 6:
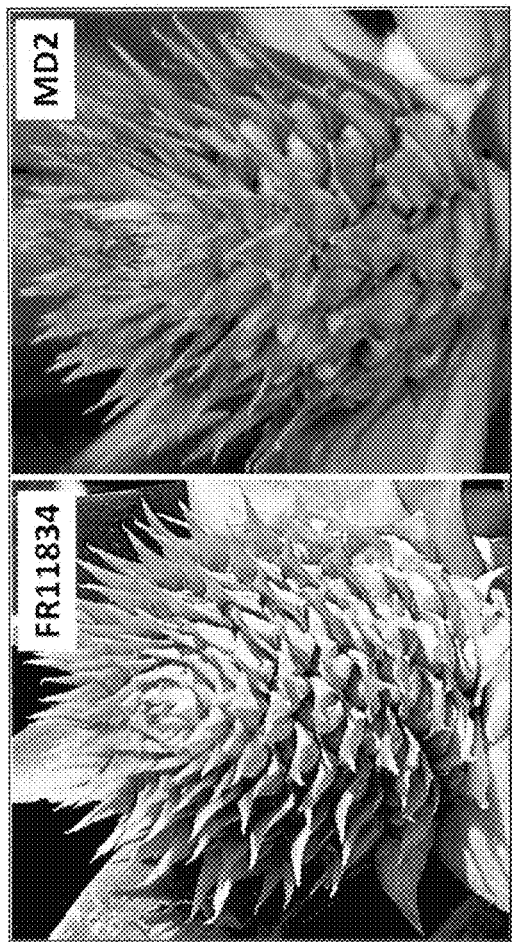

FIG. 6. Emerging inflorescence of 'FR11834' and MD-2 right before flower opening; 'FR11834' shows a distinct yellow coloration of sepals that contrasts with the reddish coloration of MD-2 sepals at early cone stage.

DETAILED BOTANICAL DESCRIPTION

The new *Ananas comosus* cultivar 'FR11834' has not been observed under all possible environmental conditions. However, the plants were grown under environmental conditions and cultural practices which approximate those generally used in commercial pineapple growing operations. The phenotype of the new cultivar may still vary depending on the environmental conditions such as temperature, humidity, light intensity, and photoperiod without any change made to the genotype of the plant.

The aforementioned photographs, together with the following observations, measurements and values describing plants of 'FR11834' variety are based on observations made under optimally fertilized and growing conditions, in the region of Limoeiro do Norte, Ceará, Brazil (latitude −5.21945833° and longitude −37.914505°), where the temperatures generally range from 15.96-38.70° C., and an annual rainfall average of 746 mm.

The color terminology and designation reported here are in accordance to the Munsell Color Notation for Plants Tissues published by Munsell Color Macbeth, a division of Kollmorgen Corporation, Baltimore, Md. USA.

The following description was made based on a population of 'FR11834' plants, the BC3 hybrid obtained through hand pollination of parental lines in 2015 and planted in 2018 and fruit harvested in 2020 and new propagules produced from this plant planted in 2020.

Plant identification: Name: *Ananas comosus* var. *comosus* 'FR11834'.

Parental lines: Selected plant (BC2) '1/2.24' backcrossed to 'MD-2'.

Origin: Conventional genetic improvement (hand pollination), through crossing and backcrossing.

Classification: Botanical: Bromeliaceae or pineapple family. Subfamily: Bromelioidae. Genus: *Ananas*. Subgenus: *comosus*. Variety: 'FR11834'.

Commercial: Bromeliad fruit plant (pineapple).

Form: Terrestrial, with overlapping, sessile leaves from a funnel-formed rosette, surrounding a composite inflorescence (during anthesis), with few or no slips in the fruit peduncle and suckers that are produced in the stem and originate subsequent crops.

General description: 'FR11834' (before anthesis).

Growth habit: Semi-erect.

Stem:

I. *General*.—Short, vertical, and covered by overlapping leaves, each leaf with a dominant axillary bud.

II. *Stem texture*.—Glabrous and fleshy.

III. *Stem size*.—A) Length (above soil level): usually between 13.90-26.00 cm at anthesis. B) Diameter between 6.90-14.00 cm at ground level to the anthesis.

IV. *Stem shape*.—Cylindrical and with a narrower diameter at the distal part.

V. *Stem color*.—Whitish in color (7.5YR 9/4 in the Munsell color chart)

Leaves:

I. *General*.—Closely overlapping sessile leaves (formed in acropetal succession) forming a dense rosette, the outline of which in longitudinal section is roughly heart shaped. The number of leaves fluctuates between 38-48 with a 5/13 phyllotaxy.

II. *Texture*.—A) Upper epidermal area: Glabrous, semirigid and channeled (or concave) except at the leaf tip. B) Lower epidermal area: Finely striated (longitudinally) and appears covered with a white layer consisting of scale like trichomes.

III. *Leaf arrangement*.—Alternate and in rosette shape.

IV. *Leaf margins*.—Flat, with rarely found irregularly spaced small deltoid cuspidate hooked spines usually located on the distal portions of leaves. Size of spines 1.95 mm.

V. *Leaf venation*.—Parallel.

VI. *Leaf shape*.—Leaves are not uniform in shape and vary with the position of the leaf on the stem. The basal or oldest leaves are lanceolate while the base is considerably expanded. There is a noticeable narrowing in width between achlorophyllous (basal) and chlorophyllous (or main portion) of the leaves. The longest or most mature leaves are lanceolate in shape, but the base is without the arcuate expansions of the preceding leaves. The remaining leaves (or center leaves of the plant rosette) are lanceolate in form with no expansion of width into the base.

VII. *Leaf size* (*to anthesis*).—A) Length: Usually between 69.0-103.0 cm for those 'D' leaves with a non chlorophyllous base that usually is between 8.0-14.0 cm in length. B) Width: Normally between 3.2-7.5 cm in the mid leaf area of the longest leaves. The expanded basal disk usually has a maximum width of 2.9-10.8 cm. C) Thickness: In the longest leaves, it usually varies between 1.80-2.60 mm at the center of the mid leaf area and decrease laterally between 1.1-1.5 mm at the margin, while becoming slightly thinner towards the tip. The expanded basal disk at the mid stem area usually has a maximum thickness of 1.94-2.80 mm at the center of the blade and tapering laterally toward margins up to 0.33-0.95 mm.

VIII. *Leaf color similar to that of 'MD2', mostly lacking anthocyanin*.—A) Upper epidermal surface: 1. General: dominant color is usually dark green. The color of the basal disk is predominantly white and light green. achlorophyllous basal disk area: commonly pale white. Mid leaf area: commonly dark green (7.5GY 4/6 in the Munsell color chart). Leaf tip area: commonly dark green (7.5GY 4/6 in the Munsell color chart). B) Lower epidermal surface (underside): General: commonly green to grayish green (10GY 6/5 in the Munsell color chart) with pale white basal disk area (N8 in the Munsell color chart).

Inflorescence (at anthesis):

I. *General*.—Flower composite from 47-93 fruitlets borne per inflorescence of a long peduncle of approximately 16.2-18.0 cm length at the apical meristem. Individual bisexual flowers that consist of three Sepals, Six Stamens, three Stigmas and three Carpels. The inflorescence is self-incompatible producing edible fruit parthenocarpically (production of fruit without fertilization of ovules).

II. *Texture*.—Glabrous and fleshy.

III. *Shape*.—Oval with slightly raised flowers with a light red to grayish red color in the crown.

IV. *Size and color*.—Comparable to specimens of *Ananas comosus* var. *comosus*. Petal size: 1.50 cm. Petal color in the apex: light purple (10P 5/10 in the Munsell color chart).

V. *Sepal size*.—0.77 cm. Sepal color: reddish brown (7.5R 5/2 in the Munsell color chart).

VI. *Floral bract's length*.—From 1.61 cm, serrated margins (with tiny spines); yellowish brown color (2.5Y 5/4 in the Munsell color chart).

Crown (at harvest):

I. *General*.—Visually one crown, composed on average of 88 leaves. Crown leaves are short, lanceolate in shape, and erect at anthesis, measuring on average 6.8 cm.

II. *Leaf arrangement*.—Alternate and in rosette shape.

III. *Leaf margins*.—Flat with smooth borders. Seldom very small spines in the tip of one leaf.

IV. *Size crown size at harvest*.—Average 16.2 cm. Weight: average 186 g. Diameter: 14.6 cm.

V. *Shape*.—Medium crown with medium width and semirigid leaves.

VI. *Attitude*.—Upright

VII. VI. *Color of the terminal crown leaves*.—A. Upper surface: Dark green color at the apex (5GY 2/2 in the Munsell color chart) and dark green at the base (5GY 2/2) in the Munsell color chart). B. Lower surface: grayish green (10GY 6/5 in the Munsell color chart).

Fruit (at harvest):

I. *Size*.—Usually with a weight between 861-2053 grams and average weight of 1191 grams. Fruit core's diameter 2.15 cm. Fruit core's color: yellow to dark yellow (7.5Y 9/6 in the Munsell color chart).

II. *Shape*.—Cylindrical with flat and medium size fruitlets. Medium-big crown with thin and semirigid leaves. Average fruit's height 12.93 cm, fruit's diameter: average 10.0 cm.

III. *How borne*.—The development of the fruit occurs from the apical meristem of the plant on a long and strong peduncle, usually between 16.2-18.4 cm length. No slips available for evaluation. 6 long peduncle bracts, with spines on the edges and of medium green to dark green color (2.5GY 6/8 in the Munsell color chart) are generally present at the base of the fruit. Color. A) Shell: commonly grayish green at early maturity (2.5GY ½ in the Munsell color chart), with yellowish brown bract (2.5Y 5/4 in the Munsell color chart). Fruit with yellow peduncle (7.5Y 9/6 in the Munsell color chart).

IV. *Fruit flesh*.—Dense, firm, medium in fiber and juiciness, emitting characteristic pineapple aroma; flesh color distinctly yellow (7.5Y 8/6 in the Munsell color chart).

V. *Brix*.—Typically, average 19.0 degrees, standing out from their parents.

VI. *Total acid levels*.—Usually between 0.59-0.72 milligrams of citric acid/ml of juice, with an average of 0.63 mg/ml.

VII. *Vitamin C content reported as ascorbic acid content*.—Regularly between 47.13 and 56.70 mg/100 ml of juice, with an average of 53.15 mg/100 ml.

VIII. *Plant/fruit resistance/susceptibility to pest and diseases*.—The plant of the new variety 'FR11834' performs very similar to 'MD-2' differentiating mainly in its resistance to *Fusarium guttiforme*. Table 2 shows the comparison of pineapple varieties 'FR11834', 'MD-2' and 'Champaka' (not patented) and their resistance to *Fusarium guttiforme*.

Others:

I. *Fertility*.—This plant is self-incompatible. This is the reason why the presence of sexual seeds is almost null. The material used for planting are suckers, fruit crowns and vitro plants.

II. *Vigor*.—This plant exhibits similar vigor as its parents, the '1/2.24' line, and the 'MD-2' variety.

III. *Yield*.—A population of this pineapple can have an agronomic yield from 85 to 147 ton/ha.

IV. *Plant use*.—The fruit will be commercialized within the fresh fruit and processed fruit for the export markets.

Summary of the special characteristics: the 'FR11834' plants present the following differences when compared to its parental lines:

A. *Resistance to fusarium guttiforme*.—MD-2 is very susceptible to this pathogen, while 'FR11834' exhibits total resistance.

B. *Yellow colored pulp*.—The backcross between the '1/2.24' backcrossed against 'MD-2', resulted in a fruit with similar shell color and yellow pulp like the 'MD-2' variety.

C. *Plant with few or no slips*.—'MD-2' variety produces between 1-3 slips per plant, and the '1/2.24' produces between 3-7 slips per plant. By comparison, 'FR11834', produces few or no slips, which may reduce cosmetic and pest problems that can be originated by the contact of the slips with the fruit.

D. *At full maturity*.—The 'FR11834' fruit achieves consistently high sugar content, brix levels being almost 2 degrees higher than those achieved by MD-2 under similar circumstances. Citric acid, and ascorbic acid are similar as those of 'MD-2' and '1/2.24' fruits.

E. *As a result of the backcross process*.—'FR11834' has acquired resistance to *Fusarium guttiforme*, just like the '1/2.24' but with an improved fruit size, pulp color, and internal quality similar to the 'MD-2'. This combination of characteristics is important to differentiate this hybrid from its parents; as shown on Table 3, when reproduced asexually, these characteristics are stable and reproducible for successive generations.

TABLE 1

Average data for select organoleptic parameters and fruit size of the 'FR11834' hybrid.

| Generation | n | Brix | Ascorbic. Acid (mg/100 ml) | Citric Acid (mg/ml) | Fruit Weight (g) | Number of slips |
|---|---|---|---|---|---|---|
| 'FR11834' | 1 | 18.1 | 56.7 | 0.72 | 2053 | 0 |
| 'MD2' | 71 | 16.3 | 61.4 | 0.95 | 1949 | 0 |

(data for 'FR11834' represent observations from the first plant evaluated when backcrossing 'MD-2' with 1/2.24 hybrid; data for 'MD2' represents the average score for 'MD2' variety in the region).

Individual plant description: The following is an overview of 'FR11834' hybrid, a new pineapple plant variety, that was developed through hybridization process in Limoeiro do Norte, Ceará, Brazil.

*Plant age*.—15.38 months after planting plus 5.32 months after forcing.

*Plant growth habit*.—Semi-upright.

*Plant diameter*.—Around 146 cm between opposite leaf tips.

*Plant height*.—127 cm above ground surface.

*Stem*.—Length. Between 13.90-26.00 cm above ground surface. Diameter. Between 6.90-14.00 cm above ground surface.

Leaves:

I. *Number*.—53 leaves.

II. *Length*.—103 cm the longest leaf.

III. *Width*.—(Largest leaves) at mid leaf (max.) 6.35 cm. Leaf piping is absent.

IV. *Thickness*.—2.15 mm along the axis.

V. *Color*.—A) Upper epidermal chlorophyllous area: Commonly dark green (7.5GY 4/6 in the Munsell color chart). B) Upper epidermal non chlorophyllous area: commonly pale white (N8 in the Munsell color chart). C) Lower epidermal area: Commonly grayish green (10GY 6/2 in the Munsell color chart). Leaf anthocyanin coloration may appear slightly on some plants.

Inflorescence:

*General*.—Composite inflorescence borne on a long peduncle at the apical meristem. The inflorescence is composed of 93 flowers, which eventually lead to an equal number of fruitlets.

TABLE 2

Petals: Description of size and texture of flowers of 'FR11834' hybrid

| Inflorescence | UPOV ID | Trait | Note |
|---|---|---|---|
| | 14 | Size of bracts (cm) | 1, 61 |
| | 15 | Petal: color of apex (purple red), base (white) | 2 |
| | 16 | Petal length (mm) | 15.0 |
| | N/A | Petal width (cm) | 0.70 |
| | N/A | Petal Height (cm) | 1.50 |
| | N/A | Petal texture | very finely textured and smooth feel |

TABLE 2-continued

| Petals: Description of size and texture of flowers of 'FR11834' hybrid | | |
|---|---|---|
| I. Reproductive organs. Description of size and shape of reproductive organs of 'FR11834' | | |
| Inflorescence | Trait | Note |
| | Style (mm) | 9.48 |
| | Stamen (mm) | 9.11 |
| | Style shape | tubular |
| | Stamen shape | tubular |
| | Style color | Base = white, top - pale purple |
| | Filament color | Filament base = white, filament top - pale purple |
| | Anther color | Pale yellow |
| | Pollen color | transparent |
| II. Peduncle. length and diameter of the peduncle of 'FR11834' hybrid are as follows. | | |
| Peduncule | UPOV ID | Trait | Note |
| | 21 | Length (cm) | 17.5 ± 1.3 |
| | 22 | Diameter (cm) | 2.4 ± 0.3 |

TABLE 3

Susceptibility to pest and diseases of different commercial varieties to *Fusarium guttiforme* ('FR11834' is resistant and 'Champaka' and 'MD2' are susceptible).

| | Pineapple Variety | | |
|---|---|---|---|
| Pest/Disease | 'FR11834' | 'MD-2' | 'Champaka' |
| *Fusarium guttiforme.* | R+ | S + | S |

The pineapple variety 'FR11834' has a post-harvest shelf life similar to 'MD-2' variety, showing similar performance in shell dehydration studies.

'FR11834' fruit general characteristics are as follows (A) a fruitlet apex which is flat; (B) the flesh density is medium; (C) the number fruitlets per syncarp is 47-93; (D) the fruitlet characteristics are as follows:

TABLE 4

| | UPOV ID | Trait | Note |
|---|---|---|---|
| Fruit | 31 | Fruit shape (cylindrical) | 3 |
| | 32 | Fruit length (cm) | 12.9 ± 4.7 |
| | 33 | Fruit diameter (cm) | 10.0 ± 1.3 |
| | 34 | Predominant color of mature eye (medium yellow) | 6 |
| | 35 | Fruit: Size (medium) | 5 |
| | N/A | Size of eye diameter width (cm) | 2.65 ± 0.1 |
| | N/A | Size of eye length (cm) | 2.65 ± 0.1 |
| | N/A | Color of immature eye (grayish green) | 4 |
| | 37 | Fruitlet apex (flat) | 2 |
| | 38 | Evenness of color of eyes (even or slightly uneven) | 1 |

I. *Shell color*.—'FR11834' shell color at mature (10YR 9/4) and immature (2.5GY 1/2) stages.

II. *Weight and shape of fruit*.—'FR11834' average fruit weight is similar to the 'MD-2', and 'Champaka'; 'FR11834' has a cylindrical shape.

III. *Ascorbic acid*.—'FR11834' has a higher content of ascorbic acid than its relative *A. comosus* cv. 'Manzana', but similar to 'MD-2' variety.

IV. *Citric acid*.—'FR11834' citric acid content is similar to 'MD-2'.

V. *Brix*.—The sugar content (measured as brix degrees) of 'FR11834' is significantly higher than that found on 'MD-2'.

VI. *Age to forcing*.—'FR11834' is vigorous and can reach forcing plant size 8-17 months after planting (shorter when using vegetative propagation material, and longer when starting with seed). Although plant development time to forcing depends on the size of planting material used and the desired plant weight at floral induction, the above figures are similar to those achieved by the 'MD-2' variety, which reaches an optimal forcing size in 8.5 months after planting when using vegetative propagation material.

VII. *Leaf spines*.—This characteristic is commonly used to differentiate pineapple plants from other varieties. The color of the leaf spines are as follows: Tip: dark green like MD2 (7.5GY 4/6 in the Munsell color chart), base: dark green like MD2 (7.5GY 4/6 in the Munsell color chart). 'FR11834' does not have conspicuous or regular thorns on the leaf like its parental '1/2.24', or its parental 'MD-2', although 'MD-2' often presents irregular thorns on the edges of the leaf blade as well.

VIII. *Fruit quality of 'FR*11834' *when compared with other pineapple varieties*.—Most pineapple varieties grown worldwide are produced for local consumption, and very few are grown for international commercialization and global distribution. The fruit characteristics bred into 'FR11834' were specifically chosen to comply with the strictest quality standards of export markets like those of North America, Europe, and Asia Pacific. As shown in Table 5, 'FR11834' compares very favorably against 'MD-2', the pineapple variety that has achieved most notoriety to date in global markets.

TABLE 5

Comparison of 'FR11834' against other varieties on some of the most important characteristics relevant to fresh fruit destined for exportation.

| Comparative characteristics of different pineapple varieties and cultivars | | | | |
|---|---|---|---|---|
| Variety/ | # Of slips | | Fruit weight (g) | |
| Cultivar[11] | Average | Range | Average | Range |
| 'FR11834'[1] | 0 | 0-1 | 1191 | 681-2053 |
| 'MD2'[2] | 1.2 | 0-3 | 1820 | 1070-2560 |
| 'Morada'[3] | 7.57 | 4-9 | 1887 | 1566-2000 |
| 'Honey Gold' (U.S. Plant Pat. No. 16,328 P3) | 1.5 | 0-3 | 1033 | 450-1678 |
| 'Champaka 153'[3] | 1.1 | | 1710 | 420-3010 |
| 'Champaka F152' | 1.5 | | 2328 | |
| 'CO-2'[4] | | 2-3 | 2059 | 1297-2590 |
| 'Singapore' | | 2-12 | 1000 | |
| 'Spanish'[5] | | | | |
| 'Sarawak'[5] | 0 | | | 2000-4000 |
| 'Mauritius'[5] | 0 | | | 500-1500 |
| 'Josephine'[6] | | | | 1100-1300 |

TABLE 5-continued

Comparison of 'FR11834' against other varieties on some of the most important characteristics relevant to fresh fruit destined for exportation.

| | | | | |
|---|---|---|---|---|
| 'Scarlett'[6] | | | | 1400-2000 |
| 'Red Spansh'[7] | | 1-3 | | 1200-2000 |
| 'T'ainung 11'[7] | 6.9 | | 991 | 733-1269 |
| 'Imperial'[8] | 9 | | 1792 | |
| 'Perolera'[8] | | 8-10 | 1800 | |
| 'Pernambuco'[9] | | | | 1000-1500 |
| 'Primavera'[9] | | 7-10 | 1300 | |
| 'Queen'[10] | 10 | | | 500-1000 |

Comparative characteristics of different pineapple varieties and cultivars

| Variety/ | Ascorbic Acid (mg/100 ml) | | Citric Acid (mg/ml) | |
|---|---|---|---|---|
| Cultivar[11] | Average | Range | Average | Range |
| 'FR11834'[1] | 53.15 | 47.13-56.70 | 0.63 | 0.59-0.72 |
| 'MD2'[2] | 53.06 | 37.00-69.06 | 0.6 | 0.36-0.84 |
| 'Morada'[3] | 20.03 | 9.90-24.90 | 0.69 | 0.58-0.86 |
| 'Honey Gold' (U.S. Plant Pat. No. 16,328 P3) | 21.14 | 14.73-37.36 | 0.98 | 0.67-1.33 |
| 'Champaka 153'[3] | 12.91 | 8.10-17.72 | 0.72 | 0.54-0.90 |
| 'Champaka F152' | | | 0.73 | |
| 'CO-2'[4] | | 30.80-55.50 | | 0.42-0.91 |
| 'Singapore' | | | | 0.50-0.60 |
| 'Spanish'[5] | | | | |
| 'Sarawak'[5] | | | | 0.30-0.65 |
| 'Mauritius'[5] | | | | 0.40-0.60 |
| 'Josephine'[6] | | | | |
| 'Scarlett'[6] | | | | |
| 'Red Spansh'[7] | | | | |
| 'T'ainung 11'[7] | | 1.40-18.50 | 0.5 | 0.40-0.6 |
| 'Imperial'[8] | | | 0.62 | |
| 'Perolera'[8] | | | 0.64 | |
| 'Pernambuco'[9] | | | | |
| 'Primavera'[9] | | | 0.51 | |
| 'Queen'[10] | 26 | | 0.56 | |

Comparative characteristics of different pineapple varieties and cultivars

| Variety/ | °Brix | |
|---|---|---|
| Cultivar[11] | Average | Range |
| 'FR11834'[1] | 19.00 | 18.1-20.7 |
| 'MD2'[2] | 15.55 | 12.9-17.2 |
| 'Morada'[3] | 13.51 | 12.2-15.1 |

TABLE 5-continued

Comparison of 'FR11834' against other varieties on some of the most important characteristics relevant to fresh fruit destined for exportation.

| | | |
|---|---|---|
| 'Honey Gold' (U.S. Plant Pat. No. 16,328 P3) | 16.18 | 14.4-18.1 |
| 'Champaka 153'[3] | 14.33 | 11.6-17.0 |
| 'Champaka F152' | 14.97 | |
| 'CO-2'[4] | | 15.0-16.7 |
| 'Singapore' | | 10.0-12.0 |
| 'Spanish'[5] | | |
| 'Sarawak'[5] | | 14.0-17.0 |
| 'Mauritius'[5] | | 15.0-17.0 |
| 'Josephine'[6] | | 17.0-22.0 |
| 'Scarlett'[6] | | 15.0-18.0 |
| 'Red Spansh'[7] | 12.00 | |
| 'T'ainung 11'[7] | 14.00 | 13.2-15.1 |
| 'Imperial'[8] | 15.80 | |
| 'Perolera'[8] | 13.10 | 14.0-16.0 |
| 'Pernambuco'[9] | | |
| 'Primavera'[9] | 13 | |
| 'Queen'[10] | | 14.0-16.0 |

(data for 'FR11834' represent observations from the first plant evaluated when backcrossing 'MD-2' with 1/2.24 hybrid; data for 'MD2' represents the average score for 'MD2' variety in the region).

[1]FR11834 fruit harvested in Brazil.

[2]Pindeco's historical data base and monthly research report April 2001.

[3]Pindeco's fruit historical data base. Pindeco's forcing plant weight data base.

[4]Plant patent 8,863.

[5]Wee, Y. C. 1972. Some common pineapple cultivars of west Malaysia. Malays Pineapple pp 7-13.

[6]Bartholomew et al. 2003 The Pineapple, Botany, Production and Uses.

[7]Chang, Ching-Chyn, 1995 Tainung No. 13. Pineapple. Jour. Agric. Res. China 44(2): 287-296.

[8]Pinto da Cunha et al. 0 abacaxizeiro. Pineapple News Issue No 10 May 2003.

[9]Pinto da Cunha et al. 0 abacaxizeiro. Py et al. The pineapple Cultivation and uses.

[10]Del Monte pineapple germplasm collection database.

[11]Cultivars are unpatented unless indicated otherwise.

REFERENCES CITED

MATOS, A. P. (2008)—Perdas causadas pela *F. guttiforme*. Disponivel em.

MATOS, A. P. & JUNEGHANS, D. T. Variedades de abacaxi resistentes a *F. guttiforme*. 2006. Cruz das Almas, BA.

Munsell Color chart for Plant Tissues. published by Munsell Color Macbeth, a division of Kollmorgen Corporation, Baltimore, Md. USA.

What is claimed is:

1. A new and distinct *Ananas comosus* plant named 'FR11834', as illustrated and described herein.

* * * * *